US006943152B1

(12) United States Patent
Audonnet et al.

(10) Patent No.: US 6,943,152 B1
(45) Date of Patent: Sep. 13, 2005

(54) DNA VACCINE-PCV

(75) Inventors: Francis Jean-Christophe Audonnet, Lyons (FR); Michel Bublot, Delmar, NY (US); Jennifer Maria Perez, East Nassau, NY (US); Catherine Elisabeth Charreyre, Saint-Laurent de Mure (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 09/586,535

(22) Filed: May 31, 2000

Related U.S. Application Data

(60) Provisional application No. 60/138,352, filed on Jun. 10, 1999.

(51) Int. Cl.[7] ........................ A61K 48/00; A61K 9/127; A01N 65/00; A01N 63/00; C12N 15/74

(52) U.S. Cl. ..................... 514/44; 424/93.1; 424/93.21; 424/450; 435/320.1; 536/23.1

(58) Field of Search ........................... 514/44; 424/93.1, 424/93.21, 450; 435/320.1; 536/23.1

(56) References Cited

U.S. PATENT DOCUMENTS

| | | | | | |
|---|---|---|---|---|---|
| 4,946,787 A | * | 8/1990 | Eppstein et al. | ......... | 435/240.2 |
| 5,106,733 A | | 4/1992 | Baker et al. | | |
| 5,459,127 A | | 10/1995 | Felgner et al. | | |
| 5,545,412 A | | 8/1996 | Eppstein et al. | | |
| 5,580,859 A | | 12/1996 | Felgner et al. | | |
| 5,703,055 A | | 12/1997 | Felgner et al. | | |
| 5,705,385 A | | 1/1998 | Bally et al. | | |
| 5,719,131 A | | 2/1998 | Harris et al. | | |
| 5,910,488 A | * | 6/1999 | Nabel et al. | | |
| 6,015,694 A | * | 1/2000 | Dubensky, Jr. et al. | .... | 435/69.3 |
| 6,019,980 A | | 2/2000 | Li et al. | | |
| 6,165,493 A | * | 12/2000 | Neurath et al. | ............. | 424/434 |
| 6,217,883 B1 | * | 4/2001 | Allan et al. | .............. | 424/202.1 |
| 6,287,856 B1 | * | 9/2001 | Poet et al. | | |
| 6,368,601 B1 | | 4/2002 | Allan et al. | | |
| 6,391,314 B1 | | 5/2002 | Allan et al. | | |
| 6,475,779 B2 | * | 11/2002 | Mathiowitz et al. | ..... | 435/320.1 |

FOREIGN PATENT DOCUMENTS

| | | |
|---|---|---|
| EP | 0 737 750 | 10/1996 |
| WO | WO 90 11092 | 10/1990 |
| WO | WO 92 05255 | 4/1992 |
| WO | WO 94 01133 | 1/1994 |
| WO | WO 94/21797 | 9/1994 |
| WO | WO 94/27435 | 12/1994 |
| WO | WO 96/34109 | 10/1996 |
| WO | WO 96 40945 | 12/1996 |
| WO | WO 98 40499 | 9/1998 |
| WO | WO 99/18214 | 4/1999 |
| WO | WO 99/29717 | 6/1999 |
| WO | WO 99/29871 | 6/1999 |
| WO | WO 00/01409 | 1/2000 |
| WO | WO 00 24428 | 5/2000 |
| WO | WO 00/77216 A2 | 12/2000 |

OTHER PUBLICATIONS

DMRIE structure, 2002.*
Meehan et al. Characterization of novel circovirus dans associated with wasting syndromes in pigs Journal of General Virologt 1998 79, 2171–2179.*
Restifo N P et al. The promises of nucleic acid vaccines, 2000, Gene Therpay, vol. 7, pp. 89–92.*
Babiuk et al.; research tool or commercial reality, 2000, Veterinary immunologya nd immunopathology, nucleic acid vaccines, vol. 76,pp. 1–23.*
Yokoyama et al. DNA immunization: Effects of vehicle and route of administration on theinduction of protective immunity., 1996, FEMS Immunology and medcal microbiology, vol. 14, pp. 221–230.*
Meehan B. M.., et al., Charecterization of novel circovirus DNAs associated with wasting syndromes in pigs. 1998, Journal of General Virology, vol. 79, pp. 2171–2179.*
Okada E. et al. Intranasal immunization of a DNA vaccine . . . immune responses against HIV–1 antigens. 1997, The Jouranl fo Immunology, vol. 159, pp. 3638–3647.*
Felgner J.H. et al., Enhanced gene delivery and mechanism studies with a novel series of cationic lipid formulations. 1994, The journal of biological chemistry, vol. 269, pp. 2550–2561.*
Mumford J. A. et al. Antigenicity and immunogenicity of equine imfleunza vacciens coantining a Carbomer adjuvant. 1994, vol. 112, pp. 421–437.*
Miller, J.S. et al., "The nucleotide sequence of RNA–1 of Indian peanut clump furovirus" Arch. Virol. 141:2301–2312, 1996.

(Continued)

*Primary Examiner*—Q. Janice Li
(74) *Attorney, Agent, or Firm*—Frommer Lawrence & Haug LLP; Thomas J. Kowalski; Judy Jarecki-Black

(57) ABSTRACT

The invention relates to immunogenic preparations or vaccines comprising, on the one hand, a plasmid encoding and expressing a gene from PCV, in particular selected from the group consisting of ORF1 of PCV-2, ORF2 of PCV-2, ORF1 of PCV-1 and ORF2 of PCV-1, and, on the other hand, an element capable of increasing the immune response directed against the product of expression of the gene, which can be a carbomer, a porcine cytokine, e.g. GM-CSF or a cationic lipid of formula in which $R_1$ is a saturated or unsaturated linear aliphatic radical having from 12 to 18 carbon atoms, $R_2$ is another aliphatic radical comprising from 2 to 3 carbon atoms, andt X is an hydroxyle ou amine group. The cationic lipid can be DMRIE, possibly coupled with DOPE.

47 Claims, 5 Drawing Sheets

OTHER PUBLICATIONS

Parker SE et al., "Plasmid DNA gene therapy: studies with the human interleukin–2 gene in tumor cells in vitro and in the murine B16 melanoma model in vivo" Cancer Gene Therapy, May–Jun 1996.

Ishii N. et al., "Cationic liposomes are a strong adjuvant for a DNA vaccine of human immunodeficiency virus type 1" AIDS Res Hum Retroviruses, Nov. 1, 1997.

Gregoriadis G. et al., "Liposome–mediated DNA vaccination" FEBS Letter, Feb. 3, 1997.

Behr, J.P., "Gene Transfer with Synthetic Cationic Amphiphiles: Prospects for Gene Therapy" Bioconjugate Chem. 5(5):382–389, 1994.

Xiang Z. et al., "Manipulation of the immune response to a plasmid–encoded viral antigen by coinoculation with plasmids expressing cytokines" Immunity, Feb. 1995.

S. Inumaru et al., Immunology and Cell Biology, (1995), vol. 73, pp. 474–476, XP–000946635, "cDNA Cloning of Porcine Granulocyte–Macrophage Colony–Stimulating Factor".

Colin J. McInnes et al., Gene, 1991, pp. 275–279, XP–002148815, "Cloning and Expression of a cDNA Encoding Ovine Granulocyte–Macrophage Colony–Stimulating Factor".

Nash RA et al., Blood 1991, XP 002133949, "Molecular cloning and in vivo evaluation of canine granulocyte–macrophage colony–stimulating factor".

H.C.J. Ertl et al., Viral Immunology, vol. 9, 1996, pp. 1–9, "Genetic Immunization".

John J. Donnelly et al., Journal of Immunological Methods, 1994, pp. 145–152 "Immunization with DNA".

Gregory Gregoriadis, Pharmaceutical Research, 1998, vol. 15. No. 5, "Genetic vaccines: strategies for optimization".

Diana Haddad et al., FEMS Immunology and Medical Microbiology 1997, pp. 193–202 Comparative study of DNA–based immunization vectors: effect of secretion signals on the antibody responses in mice.

Carl J. Wheeler et al., 1996, pp. 1–11, XP 002035803, "Converting an alcohol to an amine in a cationic lipid dramatically alters the co–lipid requirement, cellular transfection activity and the ultrastructure of DNA–cytofectin complexes".

Roberto Bei et al., Journal of Immunotherapy, 1998, pp. 159–169 "The Use of a Cationic Liposome Formulation (DOTAP) Mixed with a Recombinant Tumor–Associated Antigen to Induce Immune Responses and Protective Immunity in Mice".

Yoshifumi Watanabe et al., J. Biochem. 116, 1994, pp. 1220–1226 "Highly Efficient Transfection into Primary Cultured Mouse Hepatocytes by Use of Cation–Liposomes: An Application for Immunization".

Linda S. Klavinskis et al., J. Immunol 1999, "Intranasal Immunization with Plasmid DNA–Lipid Complexes Elicits Mucosal Immunity in the Femal Genital and Rectal Tracts".

C. Somasundaram et al., Veterinary Immunology and Immunopathology 70, 1999, pp. 277–287 "Enhanced Protective Response and Immuno–Adjuvant Effects of Porcine GM–CSF on DNA Vaccination of Pigs against Aujeszky's Disease Virus".

Jan Schultz et al., Intervirology 2000; vol. 43, pp. 197–217 "Update on Antiviral DNA Vaccine Research" (1998–2000).

Michael J. McCluskie et al., Molecular Medicine 5, 1999, pp. 287–300 "Route and Method of Delivery of DNA Vaccine Influence Immune Responses in Mice and Non–Human Primates".

Jon A. Norman et al., Vaccine, vol. 15, No. 8, pp. 801–803, 1997, " Development of Improved Vectors for DNA–Based Immunization and other Gene Therapy Applications".

K. M. Ruitenberg et al., Vaccine, vol. 17, 1999, pp. 237–244, "DNA–Mediated Immunization with Glycoprotein D of Equine Herpesvirus 1 (EHV–1) in a Murine Model of EHV–1 Respiratory Infection".

Jeong–Im Sin et al., Vaccine, vol. 15, 1997, pp. 1827–1833 "Protective Immunity Against Heterologous Challenge with Encephalomyocarditis Virus by VP1 DNA Vaccination: Effect of Coinjection with a Granulocyte–Macrophage Colony Stimulating Factor Gene".

Cho et al., Enhanced cellular immunity of hepatitis C virus nonstructural proteins by codelivery of granulocyte macrophage–colony stimulating factor gene in intramuscular DNA immunization. Vaccine 17 (1999) pp. 1135–1144.

Meehan et al., Sequence of porcine circovirus DNA: affinities with plant circoviruses. Journal of General Virology, (1997) pp. 78, 221–227.

Accession No. XP–002153285 The nucleotide sequence of RNA–1 of Indian peanut clump furovirus. 1996, Archives of Virology vol. 141, pp 2301–2312.

Accession No. XP–002153286 Plasmid DNA gene therapy: Studies with the human interleukin–2 gene in tumor cells in vitro and in the murine B16 melanoma model in vivo. Cancer Gene Therapy, 1996, vol. 3, pp 175–185.

* cited by examiner

FIG. 1

Plasmid pJP109

FIG. 2

Plasmid pJP111

FIG. 3

Plasmid pJP120

FIG. 4

Plasmid pJP121

FIG. 5

Plasmid pJP058

DNA VACCINE-PCV

RELATED APPLICATIONS

This application is based on and claims priority from U.S. application Ser. No. 60/138,352, filed Jun. 10, 1999. Mention is made of U.S. application Ser. No. 09/082,558, filed 21 May 1998, U.S. application Ser. No. 09/161,092, filed on 25 Sep. 1998, and French Application Nos. 97/12382, 98/00873, 98/03707, filed Oct. 3, 1997, Jan. 22, 1998, and Mar. 20, 1998. Each of these applications, and each document cited therein, is hereby incorporated herein by reference; and each document cited in the present application is also incorporated herein by way of reference.

BACKGROUND OF THE INVENTION

The present invention relates to plasmid constructs encoding and expressing porcine circovirus (PCV for Porcine CircoVirus) immunogens responsible for the PMWS syndrome (Porcine Multisystemic Wasting Syndrome or Post-Weaning Multisystemic Wasting Syndrome), to methods of vaccination and to DNA vaccines, as well as to methods of producing and of formulating these vaccines. All documents cited herein, and all documents cited in documents cited herein are hereby incorporated herein by reference.

PCV was originally detected as a noncytopathogenic contaminant in pig kidney cell lines PK/15. This virus was classified among the *Circoviridae* with the chicken anaemia virus (CAV for Chicken Anaemia Virus) and the PBFDV virus (Pscittacine Beak and Feather Disease Virus). These are small nonenveloped viruses (from 15 to 24 nm) whose common characteristic is to contain a genome in the form of a circular single-stranded DNA of 1.76 to 2.31 kilobases (kb). It was first thought that this genome encoded a polypeptide of about 30 kDa (Todd et al., Arch. Virol., 1991, 117: 129–135). Recent work has however shown a more complex transcription (Meehan B. M. et-al., J. Gen. Virol., 1997, 78: 221–227). Moreover, no significant homologies in nucleotide sequence or in common antigenic determinants are known between the three species of circoviruses known.

The PCV derived from PK/15 cells is considered not to be pathogenic. Its sequence is known from B. M. Meehan et al., J. Gen. Virol. 1997 (78) 221–227. It is only very recently that some authors have thought that strains of PCV could be pathogenic and associated with the PMWS syndrome (G. P. S. Nayar et al., Can. Vet. J., 1997, 38: 385–387 and Clark E. G., Proc. Am. Assoc. Swine Prac. 1997: 499–501). Nayar et al. have detected PCV DNA in pigs having the PMWS syndrome using PCR techniques.

Monoclonal and polyclonal antibodies directed against circoviruses found in pigs having the symptoms of the PMWS syndrome have been able to demonstrate differences between these circoviruses and the porcine circoviruses isolated from culture of PK-15 cells (Allan G. M. et al. Vet Microbiol., 1999, 66: 115–123).

The PMWS syndrome detected in Canada, the United States and France is clinically characterized by a gradual loss of weight and by manifestations such as tachypnea, dyspnea and jaundice. From the pathological point of view, it is manifested by lymphocytic or granulomatous infiltrations, lymphadenopathies and, more rarely, by hepatitis and lymphocytic or granulomatous nephritis (Clark E. G., Proc. Am. Assoc. Swine Prac. 1997: 499–501; La Semaine Vétérinaire No. 26, supplement to La Semaine Vétérinaire 1996 (834); La Semaine Vétérinaire 1997 (857): 54; G. P. S. Nayer et al., Can. Vet. J., 1997, 38: 385–387).

These circoviruses obtained from North America and from Europe are very closely related, with a degree of identity of more than 96% of their nucleotide sequence, whereas the degree of identity is less than 80% when the nucleotide sequences of these circoviruses are compared with those of porcine circoviruses isolated from PK-15 cells. Accordingly, two viral subgroups have been proposed, PCV-2 for the circoviruses associated with the PMWS syndrome and PCV-1 for the circoviruses isolated from the PK-15 cells (Meehan B. M. et al., J. Gen. Virol., 1998, 79: 2171–2179. WQ-A-9918214).

BRIEF SUMMARY OF THE INVENTION

The Applicant has found that plasmid constructs encoding and expressing PCV-2 immunogens can be used to immunize pigs against the PMWS syndrome.

PCV-2 immunogens can be used in combination with PCV-1 immunogens to also immunize these animals against PCV-2.

According to a less preferred mode, the PCV-1 immunogens may be used alone.

The subject of the present invention is plasmid constructs encoding and expressing a PCV-1 or PCV-2 immunogen, in particular the open reading frames (ORFs) 1 and/or 2 for PCV-1, and the ORFs 1 and/or 2 for PVC-2 (ORF means Open Reading Frame).

It goes without saying that the invention automatically covers the plasmids encoding and expressing equivalent nucleotide sequences, that is to say the sequences which change neither the functionality or the strain specificity (say strain of type 1 and strain of type 2) of the gene considered or those of the polypeptides encoded by this gene. The sequences differing through the degeneracy of the code will, of course, be included.

The PCV-2 sequences used in the examples are derived from Meehan et al. supra (Strain Imp.1010 ; ORF1 nucleotides 398–1342; ORF2 nucleotides 1381–314; and correspond respectively to ORF4 and ORF13 in U.S. Ser. No. 09/161,092 of 25 Sep. 1998 and to COL4 and COL13 in WO-A-9918214). Other PCV-2 strains and their sequences have been published in WO-A-9918214 and called Imp1008, Imp999, Imp1011-48285 and Imp1011-48121, as well as in A. L. Hamel et al. J. Virol. June 1998, vol 72, 6: 5262–5267 (GenBank AF027217) and in I. Morozov et al. J. Clinical Microb. September 1998 vol. 36, 9: 2535–2541, as well as GenBank AF086834, AF086835 and AF086836, and give access to equivalent ORF sequences.

The invention also covers the equivalent sequences in the sense that they are capable of hybridizing to the nucleotide sequence of the gene considered under high stringency conditions. Among the equivalent sequences, there may also be mentioned the gene fragments conserving the immunogenicity of the complete sequence.

The homology of the whole genome of types 1 and 2 therebetween is about 75%. For ORF1, it is about 86%, and for ORF2, about 66%. On the contrary, homologies between genomes and between ORFs inside type 2 are generally above 95%.

Are also equivalent sequences according to the present invention, for ORF1, those sequences having an homology equal or greater than 88%, in particular than 90%, preferably than 92% or 95% with ORF1 of strain Imp1010, and for ORF2, those sequences having an homology equal or greater than 80%, in particular than 85%, preferably than 90% or 95% with ORF2 of strain Imp1010.

DETAILED DESCRIPTION OF THE INVENTION

ORF1 and ORF2 according to Meehan 1998 has the potential to encode proteins with predicted molecular weights of 37.7 kD and 27.8 kD respectively. ORF3 and ORF4 (according to Meehan et al. 1998, correspond to ORF7 and ORF10 respectively in WO-A-9918214) has the potential to encode proteins with predicted molecular weights of 11.9 and 6.5 kD respectively. The sequence of these ORFs is also available in Genbank AF 055392. They can also be incorporated in plasmids and be used i accordance with the invention alone or in combination, e.g. with ORF1 and/or ORF2.

The other ORFs 1–3 and 5, 6, 8–9, 11–12 disclosed in U.S. Ser. No. 09/161,092 of 25 Sep. 1998 (COLs 1–3 and 5, 6, 8–9, 11–12 in WO-A-9918214), may be used under the conditions described here, in combination or otherwise with each other or with the ORFs 1 and 2 as defined here.

This also encompasses the use of equivalent sequences in the leaning given above, in particular those ORFs coming from various PCV-2 strains cited herein. For homology, one can precise that are equivalent those sequences which come from a PCV strain having an ORF2 and/or an ORF1 which have an homology as defined above with the corresponding ORF of strain 1010. For ORF3 according to Meehan, it can also be said that homology has to be for instance equal or greater than 80%, in particular than 85%, preferably than 90% or 95% with ORF3 of strain Imp1010. For ORF4 according to Meehan 1998, it can be equal or greater than 86%, in particular than 90%, preferably than 95% with ORF4 of strain Imp1010.

From the genomic nucleotide sequence, e.g. those dislosed in WO-A-99 18214, it is routine art to determine the ORFs using a standard software, such as MacVector®. Also, alignment of genomes with that of strain 1010 and comparison with strain 1010 ORFs allows the one skilled in the art to readily determine the ORFs on the genome for another strain (e.g. those disclosed in WO-A-99 18214). Using a software or making alignment is not undue experimentation and give directly access to equivalent ORFs.

The word plasmid is here intended to cover any DNA transcription unit in the form of a polynucleotide sequence comprising the PCV sequence to be expressed and the elements necessary for its expression in vivo. The circular plasmid form, supercoiled or otherwise, is preferred. The linear form is also included within the scope of the invention.

Figure 3:
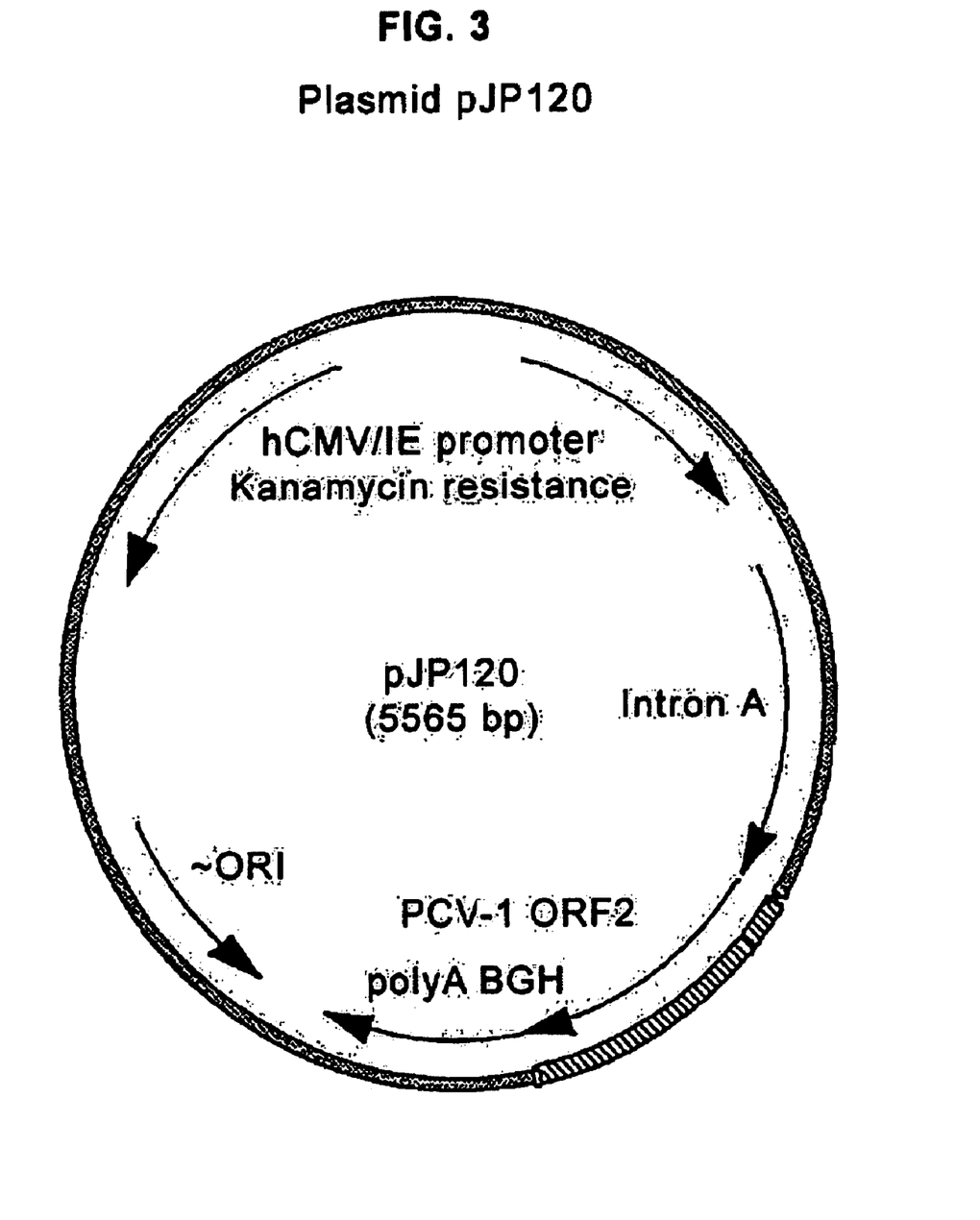
FIG. 3 depicts plasmid pJP120.
Figure 4:
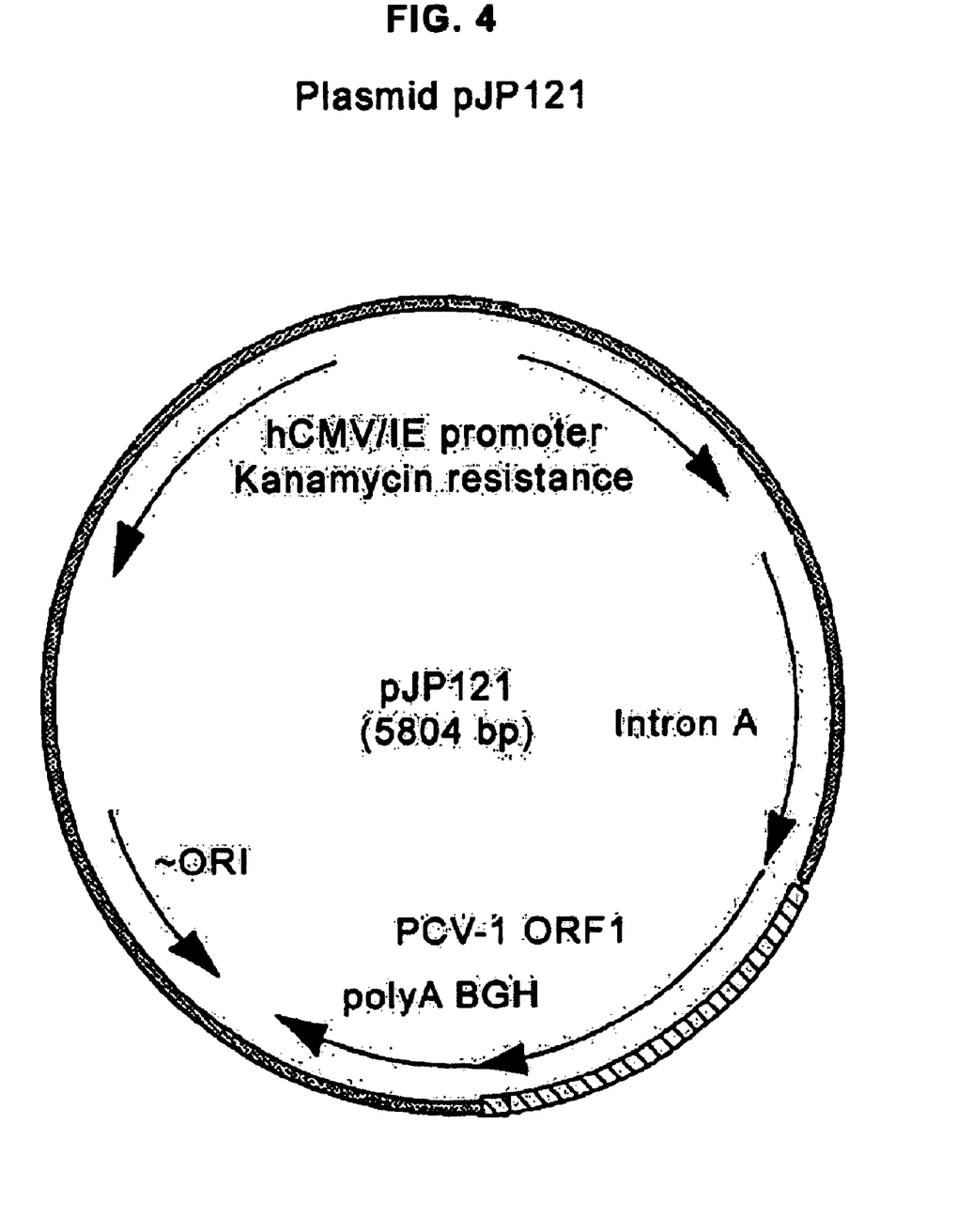
FIG. 4 depicts plasmid pJP121.

The subject of the present invention is more particularly the plasmids called pJP109 (containing the ORF2 gene of PCV-2, FIG. 1), pJP111 (containing the ORF1 gene of PCV-2, FIG. 2), pJP120 (containing the ORF2 gene of PCV-1, FIG. 3) and pJP121 (containing the ORF1 gene of PCV-1, FIG. 4).

Each plasmid comprises a promoter capable of ensuring, in the host cells, the expression of the inserted gene under its control. It is in general a strong eukaryotic promoter and in particular a cytomegalovirus early promoter CMV-IE, of human or murine origin, or optionally of other origin such as rat or guinea pig. More generally, the promoter is either of viral origin or of cellular origin. As a viral promoter other than CMV-IE, there may be mentioned the SV40 virus early or late promoter or the Rous Sarcoma virus LTR promoter. It may also be a promoter from the virus from which the gene is derived, for example the promoter specific to the gene. As cellular promoter, there may be mentioned the promoter of a cytoskeleton gene, such as for example the desmin promoter, or alternatively the actin promoter. When several genes are present in the same plasmid, they may be provided in the same transcription unit or in two different units.

The plasmids may also comprise other transcription regulating elements such as, for example, stabilizing sequences of the intron type, preferably intron II of the rabbit β-globin gene (van Ooyen et al. Science, 1979, 206: 337–344), signal sequence of the protein encoded by the tissue plasminogen activator gene (tPA; Montgomery et al. Cell. Mol. Biol. 1997, 43: 285–292), and the polyadenylation signal (polyA), in particular of the bovine growth hormone (bGH) gene (US-A-5,122,458) or of the rabbit β-globin gene.

The subject of the present invention is also immunogenic preparations and DNA vaccines comprising at least one plasmid according to the invention, encoding and expressing one of the PCV-1 or PCV-2 immunogens, preferably one of the abovementioned ORFs, in addition a veterinarily acceptable vehicle or diluent, with optionally, in addition, a veterinarily acceptable adjuvant.

The subject of the present invention is more particularly immunogenic preparations and vaccines containing at least one plasmid encoding and expressing one of the PCV-1 or PCV-2 immunogens, compositions formulated with an adjuvant, in particular a cationic lipid containing a quaternary ammonium salt of formula in which $R_1$ is a saturated or unsaturated linear aliphatic radical having from 12 to 18 carbon atoms, $R_2$ is another aliphatic radical comprising from 2 to 3 carbon atoms, and X is a hydroxyl or amine group.

Preferably it is DMRIE (N-(2-hydroxyethyl)-N,N-dimethyl-2,3-bis(tetradecyloxy)-1-propanammonium; WO-A-9634109), and preferably coupled with a neutral lipid, e.g. preferably DOPE (dioleoylphosphatidylethanolamine), to form DMRIE-DOPE. Preferably, the plasmid mixture with this adjuvant is made immediately before use and preferably, before its administration to the animal, the mixture thus produced is allowed to form a complex, for example over a period ranging from 10 to 60 minutes, in particular of the order of 30 minutes.

When DOPE is present, the DMRIE:DOPE molar ratio preferably ranges from 95:5 to 5:95, more particularly 1:1.

The plasmid:DMRIE or DMRIE-DOPE adjuvant weight ratio may range in particular from 50:1 to 1:10, in particular from 10:1 to 1:5, preferably from 1:1 to 1:2.

According to another advantageous mode of the invention, it is possible to use, as adjuvant, an adjuvant compound selected from the polymers of acrylic or methacrylic acid and the copolymers of maleic anhydride and of alkenyl derivative. The polymers of acrylic or methacrylic acid crosslinked in particular with polyalkenyl ethers of sugars or of polyalcohols are preferred. These compounds are known by the term carbomer (Pharmeuropa vol. 8; No. 2, June 1996). Persons skilled in the art can also refer to US-A-2,909,462 (incorporated by reference) describing such acrylic polymers crosslinked with a polyhydroxylated compound having at least 3 hydroxyl groups, preferably not more than 8, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol® (GF Goodrich, Ohio, USA) are particularly appropriate. They are crosslinked with an allyl saccharose or with allylpentaerythritol. Among them, there may be mentioned Carbopol® 974P, 934P and 971P.

Among the copolymers of maleic anhydride and of an alkenyl derivative, the EMAs® (Monsanto) are preferred which are copolymers of maleic anhydride and ethylene, linear or crosslinked, for example crosslinked with divinyl ether. Reference may be made to J. Fields et al. Nature, 186: 778–780, 4 Jun. 1960 (incorporated by reference). From the point of view of their structure, the polymers of acrylic or methacrylic acid and the EMAs® preferably consist of basic units of the following formula:

in which

R$_1$ and R$_2$, which are identical or different, represent H or CH$_3$ x=0 or 1, preferably x=1 y=1 or 2, with x+y=2

For the EMAs®, x=0 and y=2. For the carbomers, x=y=1.

The dissolution of these polymers in water leads to an acidic solution which will be neutralized, preferably to physiological pH, to give the adjuvant solution into which the actual vaccine will be incorporated. The carboxyl groups of the polymer are then partly in COO$^-$ form.

For this type of adjuvant, it is preferable to prepare a solution of the adjuvant, in particular of carbomer, in distilled water, preferably in the presence of sodium chloride, the solution obtained being at acidic pH. This stock solution is diluted by adding it to the required quantity (in order to obtain the desired final concentration), or a substantial part thereof, of water loaded with NaCl, preferably physiological saline (NaCl 9 g/l), in one or more portions with concomitant or subsequent neutralization (pH 7.3 to 7.4), preferably with NaOH. This solution at physiological pH will be used as it is to mix with the plasmid, in particular stored in lyophilized, liquid or frozen form.

The polymer concentration in the final vaccine composition will be 0.01% to 2% w/v, more particularly 0.06 to 1% w/v, preferably 0.1 to 0.6% w/v.

In a specific embodiment, the immunogenic or vaccine preparation comprises a plasmid or a mixture of plasmids encoding and expressing PCV-2 ORF1 and ORF2.

The invention also provides for combining the vaccination against the porcine circovirus with a vaccination against other pig pathogens, in particular those which may be associated with the PMWS syndrome. By way of example, one may cite: Aujeszky's disease virus, porcine influenza virus, PRRS, porcine parvovirus, hog cholera virus, *Actinobacillus pleuropneumoniae*.

The subject of the present invention is thus mixtures of plasmid containing at least one plasmid according to the invention and at least another plasmid encoding and expressing a porcine immunogen, selected for example from the group consisting of the glycoproteins gB and gD of the Aujeszky's disease virus (pseudorabies virus or PRV), the haemagglutinin and the nucleoprotein of the porcine influenza virus H1N1, the haemagglutinin and the nucleoprotein of the porcine influenza virus H3N2, the ORF5 and ORF3 genes of the PRRS virus of the Lelystad and USA strains, the VP2 protein of the porcine parvovirus, the E1 and E2 proteins of the hog cholera virus (HCV), the deleted apxI, apxII and apxIII genes from *Actinobacillus pleuropneumoniae* (see for the plasmids for example WO-A-9803658).

These mixtures of plasmids are taken up in a veterinarily acceptable vehicle or diluent, with optionally, in addition, a veterinarily acceptable adjuvant as described above, thus forming immunogenic preparations or multivalent DNA vaccines. These preparations or multivalent vaccines may in particular be advantageously formulated with a cationic lipid as described above, in particular DMRIE, and preferably coupled with a neutral lipid, DOPE, to form the DMRIE-DOPE.

The preparations or monovalent or multivalent DNA vaccines according to the invention, formulated or otherwise with an adjuvant as described above, may also be advantageously supplemented with a cytokine preferably of porcine origin, in particular porcine GM-CSF. This addition of porcine GM-CSF (granulocyte macrophage—colony stimulating factor; Clark S. C. et al. Science 1987, 230: 1229; Grant S. M. et al. Drugs, 1992, 53: 516) may be carried out in particular by incorporating into the preparation or into the vaccine either porcine GM-CSF protein, or a plasmid encoding and expressing the porcine GM-CSF gene (Inumaru S. and Takamatsu H. Immunol. Cell. Biol., 1995, 73: 474–476). Preferably, the porcine GM-CSF gene is inserted into a plasmid different from those encoding the PCV immunogens or the other porcine immunogens.

Figure 5:
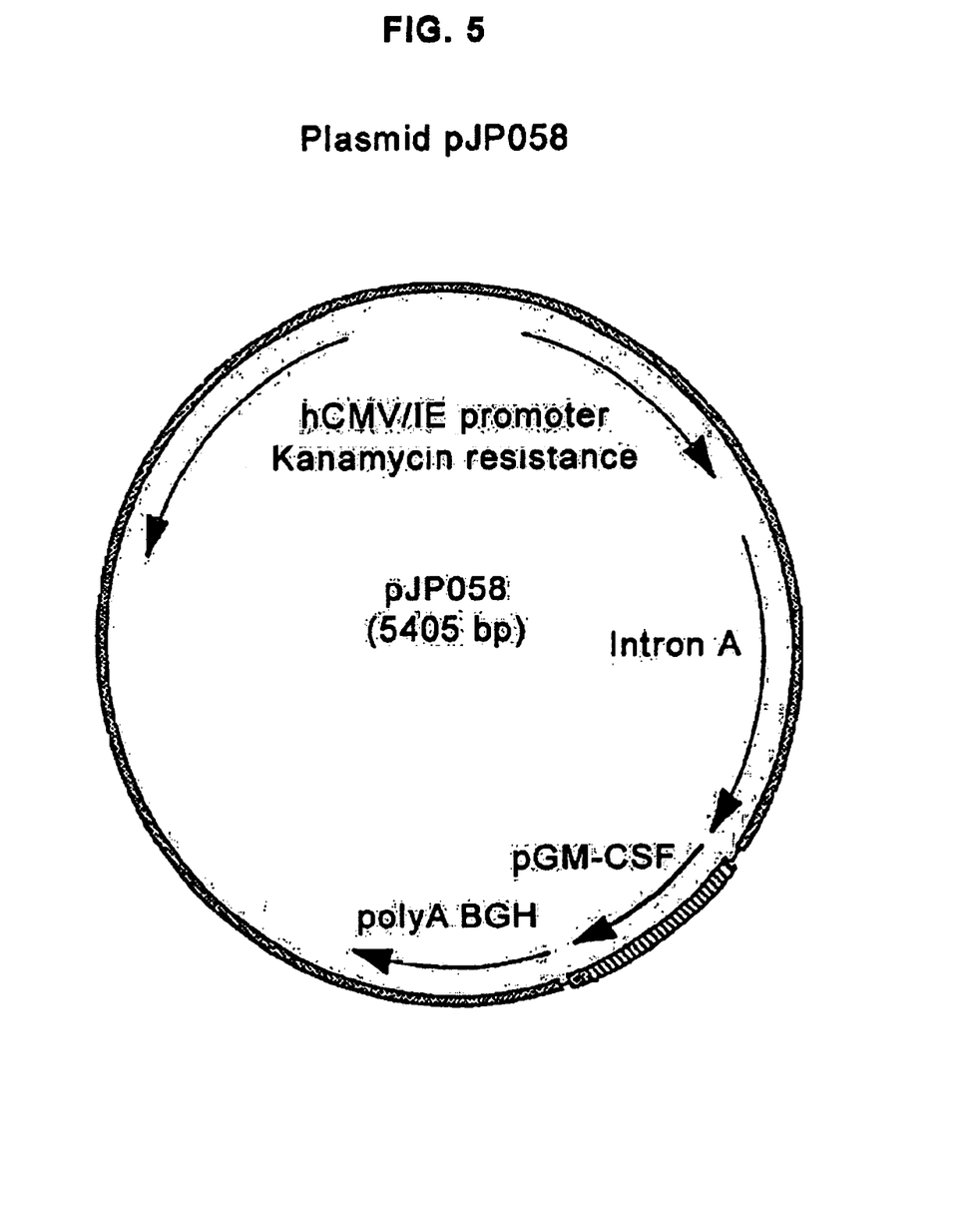
FIG. 5 depicts plasmid pJP058.

In particular, the plasmid encoding and expressing the porcine GM-CSF may be the plasmid pJP058 (FIG. 5).

The immunogenic preparations and the monovalent or multivalent DNA vaccines according to the invention may also be combined with at least one conventional vaccine (attenuated live, inactivated or subunit) or recombinant vaccine (viral vector) directed against at least one porcine pathogen which is different or identical. The invention provides in particular for the combination with adjuvant-containing conventional vaccines (attenuated live, inactivated or subunit). For the inactivated or subunit vaccines, there may be mentioned those containing in particular alumina gel alone or mixed with saponin as adjuvant, or those formulated in the form of an oil-in-water emulsion.

The subject of the present invention is also a method of immunization which makes it possible to induce an immune response in pigs towards the circoviruses according to the invention. Its subject is in particular a method of vaccination which is effective in pigs. These methods of immunization and vaccination comprise the administration of one of the preparations or of one of the monovalent or multivalent DNA vaccines as described above. These methods of immunization and vaccination comprise the administration of one or more successive doses of these preparations or DNA vaccines. The preparations and DNA vaccines may be administered, in the context of this method of immunization or of vaccination, by various routes of administration proposed in the prior art for polynucleotide vaccination, in particular the intramuscular and intradermal routes, and by means of known administration techniques, in particular injections with a syringe having a needle, by liquid jet (Furth et al. Analytical Bioch., 1992, 205: 365–368) or by projection of gold particles coated with DNA (Tang et al. Nature, 1992, 356: 152–154).

This method not only allows for administration to adult pigs, but also to the young and to gestating females; in the latter case, this makes it possible, in particular, to confer passive immunity onto the newborns (maternal antibodies). Preferably, female pigs are inoculated prior to breeding; and/or prior to serving, and/or during gestation. Advantageously, at least one inoculation is done before serving and it is preferably followed by an inoculation to be performed during gestation, e.g., at about mid-gestation (at about 6–8 weeks of gestation) and/or at the end of gestation (at about 11–13 weeks of gestation). Thus, an advantageous regimen is an inoculation before serving and a booster inoculation during gestation. Thereafter, there can be reinoculation before each serving and/or during gestation at about mid-gestation and/or at the end of gestation. Preferably, reinoculations are during gestation.

Piglets, such as piglets from vaccinated females (e.g., inoculated as herein discussed), are inoculated within the first weeks of life, e.g., inoculation at one and/or two and/or three and/or four and/or five weeks of life. Preferably, piglets are first inoculated within the first week of life or within the third week of life (e.g., at the time of weaning). Advantageously, such piglets are then boosted two to four weeks later.

The quantity of DNA used in the vaccines according to the present invention is between about 10 μg and about 2000 μg, and preferably between about 50 μg and about 1000 μg. Persons skilled in the art will have the competence necessary to precisely define the effective dose of DNA to be used for each immunization or vaccination protocol.

The dose volumes may be between 0.5 and 5 ml, preferably between 2 and 3 ml.

A preferred method of immunization or of vaccination consists in the administration of the DNA vaccines according to the invention by the intramuscular route.

The invention will now be described in greater detail with the aid of nonlimiting exemplary embodiments, taken with reference to the drawing, in which:
Sequence Listing SEQ ID
SEQ ID No. 1: oligonucleotide JP779
SEQ ID No. 2: oligonucleotide JP780
SEQ ID No. 3: oligonucleotide JP781
SEQ ID No. 4: oligonucleotide JP782
SEQ ID No. 5: oligonucleotide JP783
SEQ ID No. 6: oligonucleotide JP784
SEQ ID No. 7: oligonucleotide JP785
SEQ ID No. 8: oligonucleotide JP786
SEQ ID No. 9: oligonucleotide RG972
SEQ ID No. 10: oligonucleotide RG973

EXAMPLES

PCV-2 strains useful for cloning ORFs are for instance strains deposited at the ECACC and having the accession numbers V97100219 (Imp1008), V97100218 (Imp1010) and V97100217 (Imp999) (wich were deposited on Oct. 2, 1997), V98011608 (Imp1011-48285) and V98011609 (Imp1011-48121) (which were deposited on Jan. 16, 1998)

These examples are constructed using strain Imp1010. The one skilled in the art is able to adapt the process to other PCV-2 strains.

Example 1
Construction of the Plasmid pJP109

The plasmid pGEM7Z-Imp1010 Stoon-EcoRI No. 14 containing the genome of the PCV-2 virus in the form of an EcoRI fragment (B. Meehan et al. J. Gen. Virol. 1998. 79 2171–2179) was digested with EcoRI in order to isolate, after agarose gel electrophoresis, the EcoRI-EcoRI fragment of 1768 base pairs (bp). This fragment was self-ligated.

Figure 1:
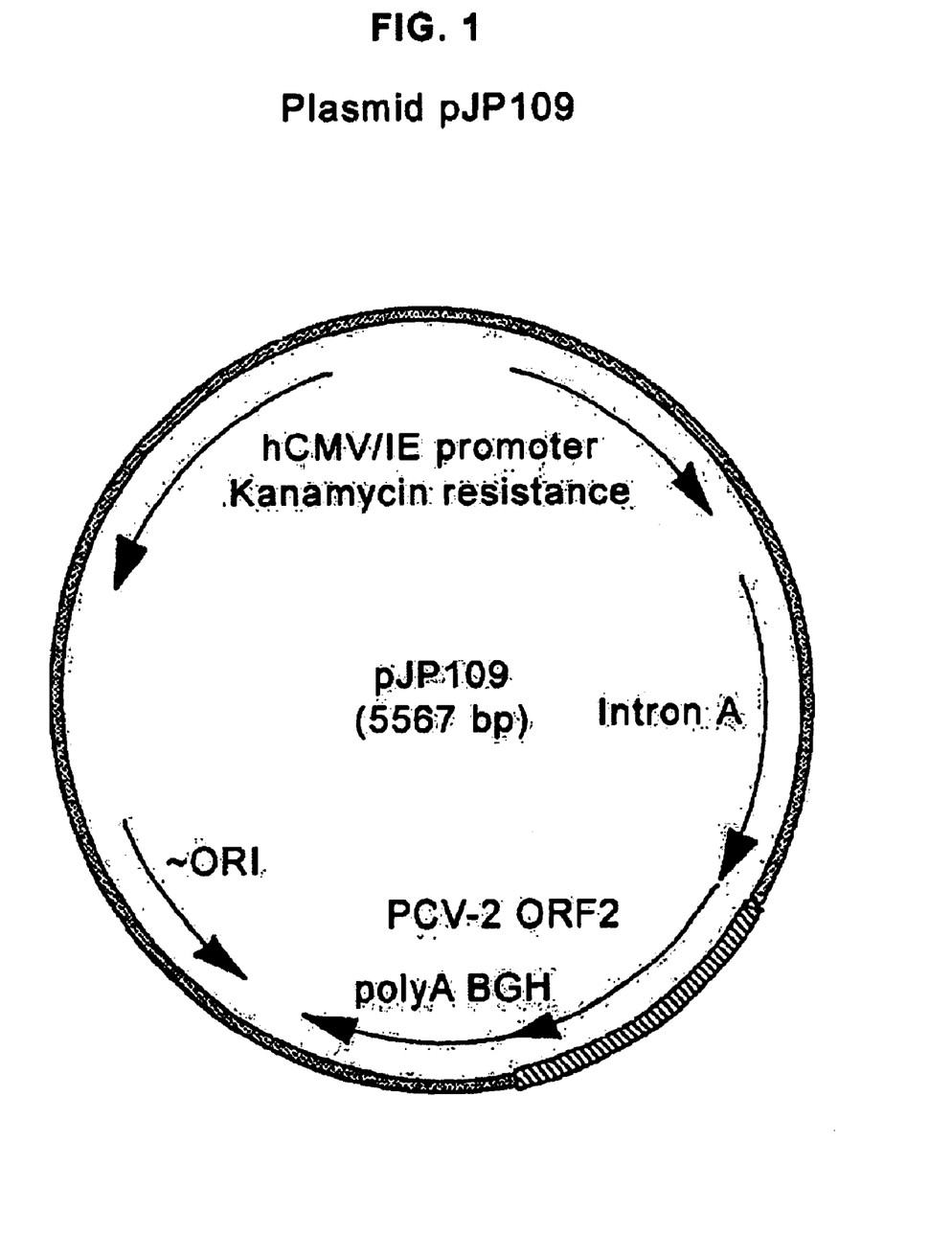
FIG. 1 depicts plasmid pJP109.

The ORF2 gene of the PCV-2 virus strain 1010-Stoon (B. Meehan et al. J. Gen. Virol. 1998. 79. 2171–2179; GenBank sequence accession No. AF055392) was amplified, using the template consisting of the self-ligated EcoRI-EcoRI fragment, by the polymerase chain reaction (PCR) technique with the following oligonucleotides:
JP779 (SEQ ID NO: 1) (35 mer):
5'CATCATCATGTCGACATGACGTATCCAAGGA-GGCG3'
and JP780 (SEQ ID NO: 2) (36 mer):
5'TACTACTACAGATCTTTAGGGTTTAAGTGG-GGGGTC3'
in order to cenerate a 730 bp PCR fragment. This fragment was digested with SalI and BglII in order to isolate, after agarose gel electrophoresis, the 715 bp SalI-BglII restriction fragment. This fragment was then ligated with the plasmid pVR1012 (Hartikka J. et al. Human Gene Therapy. 1996. 7. 1205–1217), digested beforehand with SalI and BglII, to give the plasmid pJP109 (5567 pb) (FIG. 1).

Example 2
Construction of the Plasmid pJP111

Figure 2:
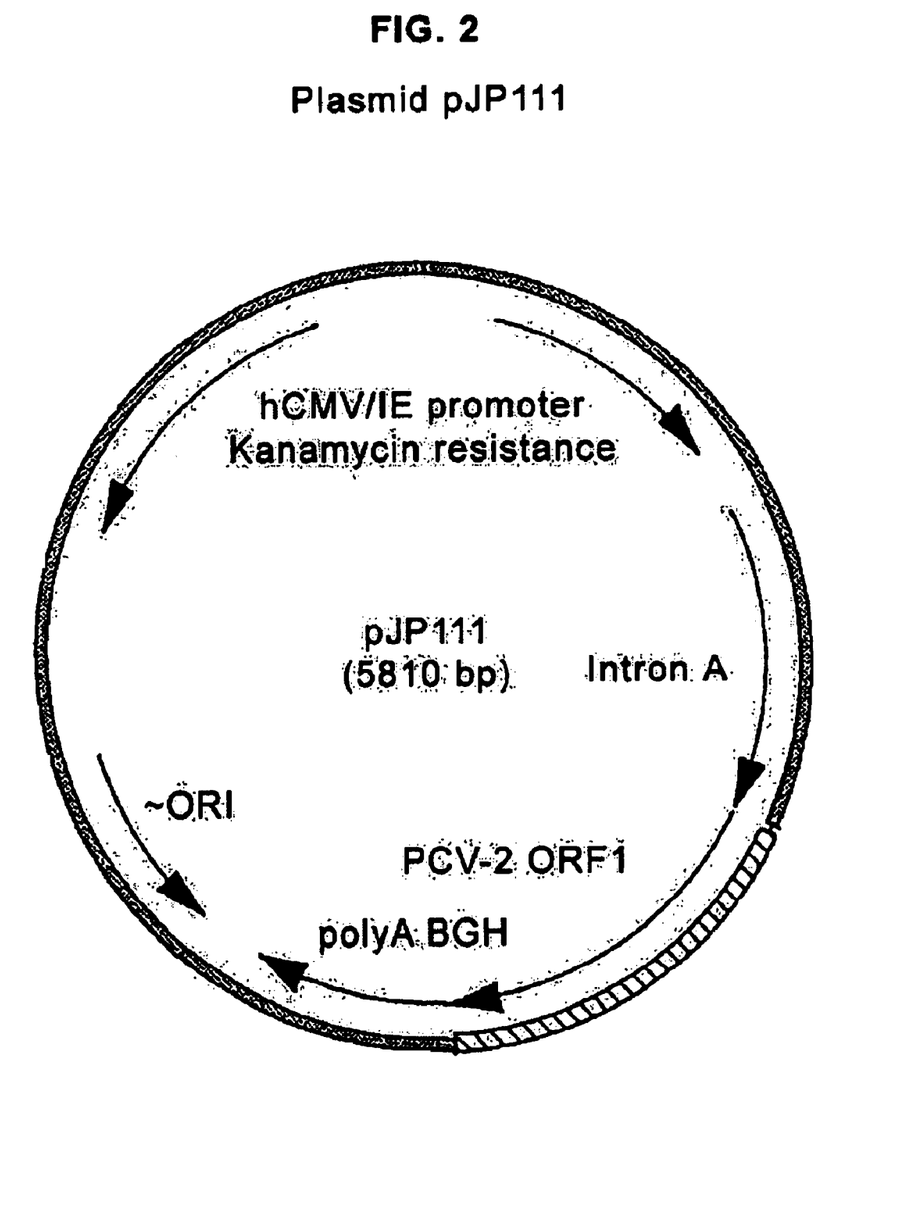
FIG. 2 depicts plasmid pJP111.

A polymerase chain reaction was carried out with the plasmid pGem7Z-Imp1010-Stoon (see Example 1) (B. Meehan et al. J. Gen. Virol. 1998. 79. 2171–2179), and the following oligonucleotides: JP781 (SEQ ID NO: 3) (35 mer):
5'CATCATCATGTCGACATGCCCAGCAAGAA-GAATGG3'
and JP782 (SEQ ID NO: 4) (36 mer):
5'TACTACTACAGATCTTCAGTAATTTATTTC-ATATGG3'
in order to generate a 970 bp PCR fragment containing the ORF1 gene of the PCV-2 virus. This fragment was digested with SalI and-BglII in order to isolate, after agarose gel electrophoresis, the 955 bp SalI-BglII restriction fragment. This fragment was then ligated with the plasmid pVR1012 (Example 1) to give the plasmid pJP111 (5810 bp) (FIG. 2).

Example 3
Construction of the Plasmid pJP120 (PCV-1 ORF2)

A polymerase chain reaction was carried out with the plasmid pPCV1 (B. Meehan et al. J. Gen. Virol. 1997. 78. 221–227), and the following oligonucleotides;
JP783 (SEQ ID NO 5) (35 mer)
5'CATCATCATGTCGACATGACGTGGCCAAGGAG-GCG3'
and JP784 (SEQ ID NO: 6) (40 mer):
5'TACTACTACAGATCTTTATTTATTTAGAGGGTCT-TTAGG3'
in order to generate a 730 bp PCR fragment containing the ORF2 gene of the PCV-1 virus (PK-15 strain, GenBank sequence accession No. U49186). This fragment was digested with SalI and BglII in order to isolate, after agarose gel electrophoresis, the 715 bp SalI-BglII restriction fragment. This fragment was then ligated with the plasmid pVR1012 (Example 1) to give the plasmid pJP120 (5565 bp) (FIG. 3).

Example 4
Construction of the Plasmid pJP121 (PCV-1 ORF1)

The plasmid pPCV1 containing the PCV1 virus genome in the form of a PstI fragment (B. Meehan et al. J. Gen. Virol. 1997, 78, 221–227) was digested with PstI in order to isolate, after agarose gel electrophoresis, the 1759 base pair (bp) PstI-PstI fragment. This fragment was self-ligated.

The ORF1 gene of the PCV-1 virus strain PK-15 (B. Meehan et al. J. Gen. Virol. 1997, 78, 221–227; GenBank sequence accession No. U49186) was amplified, using the template consisting of the self-ligated PstI-PstI fragment, by the polymerase chain reaction (PCR) technique with the following oligonucleotides:
JP785 (SEQ ID NO: 7) (35 mer):
5'CATCATCATGTCGACATGCCAAGCAAGAA-AAGCGG3'
and JP786 (SEQ ID NO: 8) (36 mer):
5'TACTACTACAGATCTTCAGTAATTTATTTTAT-ATGG3'
in order to generate a 965 bp PCR fragment containing the ORF1 gene of the PCV-1 virus (strain PK-15). This fragment was digested with SalI and BglII in order to isolate, after agarose gel electrophoresis, the 946 bp SalI-BglII restriction fragment. This fragment was then ligated with the plasmid pVR1012 (Example 1) to give the plasmid pJP121 (5804 bp) (FIG. 4).

Example 5
Construction of the Plasmid pJP058 (expressing porcine GM-CSF)

Pig blood was collected over a tube containing EDTA by taking blood from the jugular vein. The mononucleated cells were harvested by centrifugation on a Ficoll gradient and then cultured in vitro in RPMI 1640 medium (Gibco-BRL) and stimulated by addition of concanavaline A (Sigma) at a final concentration of about 5 $\mu$g/ml in the culture medium. After 72 hours of stimulation, the lymphoblasts were harvested and the total RNA of these cells was extracted with the extraction kit "Micro-Scale Total RNA Separator Kit" (Clontech) following the manufacturer's recommendations. A reverse transcription reaction, carried out with the aid of the kit "1st-Strand cDNA Synthesis Kit" (Perkin Elmer), followed by a polymerase chain reaction, was carried out on the total RNA extracted from these porcine lymphoblasts with the following oligonucleotides:
RG972 (33 mer): (SEQ ID No: 9)
5'TATGCGGCCGCCACCATGTGGCTGCAGAACCTG3'
and RG973 (34 mer): (SEQ ID No: 10)
5'TATGCGGCCGCTACGTATCACTTCTGGGCTGGTT3'
in order to generate a PCR fragment of about 450 base pairs (bp). This fragment was digested with NotI in order to isolate, after agarose gel electrophoresis, the 450 bp NotI-NotI fragment. This fragment was then ligated with the plasmid pVR1012 (Example 1), preferably digested with NotI and dephosphorylated, to give the plasmid pJP058 (5405 bp) (FIG. 5). The sequence of the PGM-CSF gene cloned into the plasmid pJP058 was checked and found to be identical to that available in the GenBank database (accession No. D21074).

Example 6
Production of the Purified Plasmids for the Vaccination of Pigs

*Escherichia coil* K12 bacteria (strains DH10B or SCS1) were transformed with the plasmids pJP109, pJP111, pJP058, pJP120 and pJP121 of Examples 1 to 5 supra. The five transformed clones obtained respectively with these five plasmids were then cultured separately, with shaking at +37° C., in Luria-Broth (LB) medium. The bacterial cultures were harvested at the end of the exponential phase and the plasmids were extracted according to the alkaline lysis technique. The extracted plasmids were then purified on a caesium chloride gradient according to the technique described by Sambrook et al. (Molecular Biology: A Laboratory Manual, 2nd Edition, 1989, Cold Spring Harbor Laboratory, Cold Spring Harbor, N.Y.). After final extraction of ethidium bromide and precipitation in the presence of absolute ethanol, the purified plasmids were resuspended in TE buffer (1 mM Tris/EDTA, pH 8.0) in order to obtain stock solutions containing 2 mg of plasmid per ml. These stock solutions are stored at −20° C. before use.

Example 7
Control of the Expression of ORFs 1 and 2 of the PCV-2 Virus

In order to control the products of expression of the PCV-2 ORF2 and PCV-2 ORF1 genes, cloned respectively into the plasmids pJP109 and pJP111, these plasmids were transfected into CHO-K1 (Chinese Hamster Ovary) cells (ATCC No. CCL-61) with the Lipofectamine Plus® transfection kit (Gibco-BRL, Catalogue# 10964-013), following the manufacturer's recommendations for use. 48 hours after transfection, the transfected cells are washed and fixed with a 95% glacial acetone solution for 3 minutes at room temperature. Five monoclonal antibodies specific for the PCV-2 ORF1 proteins (F199 1D3GA and F210 7G5GD) and ORF2 proteins (F190 4C7CF, F190 2B1BC and F190 3A8BC) were used as first antibodies. An anti-mouse IgG conjugate, labelled with Cy3, was used to reveal the specific labelling. A PCV-2 specific fluorescence was observed with the 3 PCV-2 ORF2 monoclonals in the cells transfected with the plasmid pJP109, but not in those transfected with the plasmid pJP111. In contrast, a PCV-2 specific fluorescence was observed with the two PCV-2 ORF1 monoclonals in the cells transfected with the plasmid pJP111, but not in those transfected with the plasmid pJP109. No fluorescence was detected with the PCV-2 monoclonals in CHO cells transfected with the plasmid pVR1012 alone or in the nontransfected CHO cells. The same expression result was obtained with a polyclonal serum specific for the PCV-2 virus. In this case, a fluorescein-labelled anti-pig IgG conjugate was used to detect the specific fluorescence. No fluorescence was detected with this polyclonal serum in CHO cells transfected with the plasmid pVR1012 alone or in the nontransfected CHO cells.

Example 8
Vaccination of Pigs with Naked DNA
8.1. One-day-old Piglets

Groups of piglets obtained by Caesarean on D0 of the protocol, are placed in an isolating unit. These piglets are vaccinated at the age of 2 days by the intramuscular route with various vaccinal solutions of plasmid. The vaccinal solutions are prepared by diluting the stock solutions in sterile physiological saline (0.9% NaCl).

The piglets are vaccinated:
either with the plasmid pJP109 alone
or with the mixture of the plasmids pJP109 and pJP111
or with the mixture of the plasmids pJP109 and pJP058
or with the mixture of the plasmids pJP109, pJP111 and pJP058

The vaccinal solutions comprise 500 $\mu$g of each plasmid. Volume: The vaccinal solutions are injected by the intramuscular route in a total volume of 2 ml. In practice, given the age of the piglets on vaccination (1–2 days), 1 injection of 1 ml is given on each side of the neck (=2×1 ml).

Two injections of vaccine are carried out at two weeks' interval, that is to say on days D2 and D14 of the protocol.

A challenge is made on D21 of the protocol by oronasal administration of a viral suspension of a virulent PCV-2 strain. The piglets are then monitored for 3 weeks for the appearance of specific clinical signs of post-weaning multisystemic wasting syndrome in piglets. The signs which are monitored are:

rectal temperature: daily measurement for the first 14 days, then two measurements during the 3rd week following the challenge.

Weight; weighing of the piglets just before the challenge then once per week during the 3 weeks following the challenge.

Collection of blood samples to test for viremia and antibodies: blood samples taken on D2, D14, D21, D28, D35 and D42.

Autopsy: on D42, the surviving pigs are humanely killed and undergo autopsy to search for anatomicopathological lesions and to make histological preparations from the liver, the lymph nodes, the spleen, the kidneys and the thymus to search for lesions in these tissues.

8.2. 5–7-week Old Piglets 5- to 7-week old piglets, no longer having maternal antibodies specific for the PCV-2 virus are vaccinated by the intramuscular route:
either with the plasmid pJP109 alone,
or with the mixture of the plasmids pJP109 and pJP111
or with the mixture of the plasmids pJP109 and pJP058
or with the mixture of the plasmids pJP109, pJP111 and pJP058 the vaccinal doses are the same as those indicated in Example 8.1 (500 µg per plasmid). The vaccinal solutions are injected by the intramuscular route in a volume of 2 ml (a single administration of 2 ml, into the neck muscles).

Two vaccinations are performed at 21 days' interval in (D0 and D21). A challenge is made 14 days after the last vaccination (D35) by intramuscular administration of a viral suspension of a virulent PCV-2 strain.

The pigs are then monitored for 8 weeks for the occurrence of specific clinical signs of the post-weaning multisystemic wasting syndrome in piglets. The clinical monitoring of the piglets after the challenge is identical to that described in Example 8.1 except that the total duration of observation is this time 8 weeks.

Example 9

Vaccination of Pigs with DNA Formulated with DMRIE-DOPE

It is possible to use, in place of the naked plasmid DNA solutions described in Example 8, solutions of plasmid DNA formulated with DMRIE-DOPE. A DNA solution (containing one or more plasmids according to Example 6) at 1 mg/ml is prepared in 0.9% NaCl. A DMRIE-DOPE solution at 0.75 mM is prepared by taking up a lyophilisate of DMRIE-DOPE in a suitable volume of sterile distilled water.

The formation of the plasmid DNA-cationic lipid complexes is achieved by diluting, in equal parts, the DMRIE-DOPE solution at 0.75 mM with the DNA solution at 1 mg/ml in, 0.9% NaCl. The DNA solution is introduced gradually, with the aid of a syringe mounted with a 26G needle, along the wall of the vial containing the cationic lipid solution so as to avoid the formation of foam. Gentle shaking is carried out as soon as the two solutions have been mixed. A composition comprising 0.375 mM DMRIE-DOPE and 500 µg/ml of DNA is finally obtained.

It is desirable for all the solutions used to be at room temperature for all the operations described above. The DNA/DMRIE-DOPE complex formation is performed at room temperature for 30 minutes before immunizing the pigs.

The pigs are then vaccinated according to the conditions described in Examples 8.1. and 8.2.

Example 10

Vaccination of Piglets and Results

Groups of 3 or 4 piglets, caesarian-derived day 0 are placed into isolators. The piglets are vaccinated day 2 either with pJP109 alone or with pJP109 and pJP111 plasmids mixture and with a physiological solution for the control group. Each plasmid is diluted in sterile physiological solution (NaCl 0,9%) at 250 µg/ml final concentration. A 2 ml volume is injected by intramuscular route in two points of 1 ml (1 point each side of the neck). A second injection of vaccine or placebo is administered day 14. Vaccination with DNA is well tolerated by piglets and no evidence for adverse reaction to vaccination is noted. The piglets are challenged day 21 by oronasal administration of PCV-2 viral suspension, 1 ml in each nostril. After challenge piglets are weighed once a week. Rectal temperatures are recorded on days 17, 21, 22, 24, 27, 29, 31, 34, 37, 41, 44. Day 44 fecal swabs are collected from each piglet for PCV-2 shedding. The virus is detected and quantified by quantitative PCR. Day 45 necropsies are performed and tissue samples are collected for virus isolation.

Clinical Symptoms

There is no significant difference for the mean body weight gains or the mean body temperatures between groups.

Necropsy Lesions:

The only gross finding noted in pigs at termination is bronchial lymphadenopathy. The lesions are scored according the following criteria.

0=no visible enlargement of lymph nodes

1=mild lymph nodes enlargement, restricted to bronchial lymph nodes

2=moderate lymph nodes enlargement, restricted to as bronchial lymph nodes

3=severe lymph nodes enlargement, extended to bronchial submandibullar prescapsular and inguinal lymph nodes.

std is an abbreviation for standard deviation N is for number of animals in each group

| Groups | Lymphadenopathy scores | | |
|---|---|---|---|
| | mean | std | N |
| pJP109 | 1.2 | 1.3 | 4 |
| pJP109 + pJP111 | 2.0 | 1.7 | 3 |
| controls | 3.0 | 0.0 | 3 |

N =number of piglets in each group

A reduction of the lymph node lesions is observed in 3 out 4 piglets immunized with pJP109 and 1 out 3 piglets immunized with pJP109 and pJP111 plasmids mixture. This difference is not significant (p>0.05) due to the high value of the standard deviations (std)

Virus Load in Lymph Nodes Tissues:

Quantitative virus re-isolation is performed on tissue homogenates prepared from bronchial and mesenteric lymph nodes.

The data presented correspond to the virus titers in tissue homogenates after transformation in $\log_{10}$.

PCV-2 titers

| Groups | Bronchial LN | | Mesenteric LN | | |
|---|---|---|---|---|---|
| | mean | Std | mean | std | N |
| PJP109 | 0.9 | 0.8 | 0.9 | 0.8 | 4 |
| PJP109 + pJP111 | 0.7 | 0.6 | 0.2 | 0.2 | 3 |
| Controls | 2.0 | 1.1 | 1.8 | 1.1 | 4 |

Bronchial lymph nodes seem to contain the most infectious virus. A reduction of the viral load is observed in bronchial and mesenteric lymph nodes from piglets immunized with either pJP109 or pJP109+pJP111 plasmids mixture. This reduction is significant ($p \leq 0.05$ for the plasmids mixture.

Viral Excretion:
Post challenge fecal swabs are assessed for schedding PCV-2 by PCR based on amplification of PCV-2 or f2. Each assay is performed in triplicate on 2 ml of sample. Unvaccinated controls are negative for PCV-2 prior challenge and positive after challenge confirming the validity of the PCR assay.

Value are expressed as $\log_{10}$ (number of molecules of PCV-2 DNA in 2 µl sample).

$\log_{10}$ number of PCV-2 DNA molecules

| Groups | mean | std | N |
|---|---|---|---|
| pJP109 | 3.3 | 0.3 | 4 |
| pJP109 + pJP111 | 2.9 | 0.7 | 3 |
| Controls | 3.6 | 0.6 | 4 |

The differences between groups are not significant ($p > 0.05$).

2$^{nd}$ Experiment: DMRIE/DOPE 14 day-old conventional piglets (8 per group) are immunized with 2 administrations of the pJP109 and pJP111 plasmids mixture formulated with DMRIE DOPE day 0 and day 20. For each administration 2 ml are injected by intramuscular route on the side of the neck behind the ear. The vaccine composition is 250 µg for each plasmid/ml of physiological solution (0,9% NaCl) and 0.375 mM DMRIE DOPE.

For control group piglets are injected with the physiological solution.

Day 32 the piglets are challenged by oronasal route, introducing 5 ml of PCV-2 viral suspension at a $10^{5.8}$ TCID50/ml titer with a syringe in each nostril.

The piglets are monitored for clinical symptoms, prostration, vomiting, dyspnea, cough, anorexia and hyperthermia (rectal temperature is recorded every day during 28 days post challenge) slower growth (piglets are weighed days 32, 40, 46, 53, 60). The symptoms are scored according the following criteria: Annex1 (The score for one piglet is equal to the sum of the scores corresponding to the different days of observation)

Day 60 necropsies are performed and the lesions are scored according the following criteria: Annex2 (The score for one piglet is equal to the sum of the scores corresponding to each organ observed).

Tissue samples are collected, in particular lymph nodes. Rectal swabs are collected days 32, 39, 42, 46, 49, 53, 56, 60 to follow viral excretion.

Clinical Symptoms:
A significant reduction of the clinical symptoms is observed in the group of immunized piglets compared to controls. In the control group 1 piglet died with PMWS symptoms and none in the vaccinated group.

| | Clinical scores | | |
|---|---|---|---|
| Groups | mean | std | N |
| Vaccinated | 13.5 | 7.1 | 8 |
| Controls | 29.3 | 15.6 | 8 |

($p < 0.01$ Kruskal-Wallis test)

A significant reduction of the duration of the post challenge hyperthermia is observed in the group of immunized piglet ($p \leq 0.05$).

| | Duration (days) of rectal temperature $\geq 40°$ C. | | |
|---|---|---|---|
| Groups | mean | std | N |
| Vaccinated | 1.9 | 2.0 | 8 |
| Controls | 8.4 | 3.9 | 8 |

The daily weight gain post challenge is not significantly different between vaccinated and control groups.

Necropsy Lesions:
A significant reduction of the lesions is observed in the immunized piglets compared to controls in particular for lymphadenopathy ($p \leq 0.05$).

Global lesions and lymphadenopathy scores

| Groups | mean | std | N |
|---|---|---|---|
| Global lesions | | | |
| Vaccinated | 7.6 | 3.3 | 8 |
| Controls | 13.1 | 7.5 | 8 |
| Lymph node scores | | | |
| Vaccinated | 3.1 | 2.7 | 8 |
| Controls | 5.7 | 2.9 | 8 |

Virus Load in Lymph Nodes Tissues:
The virus load in mesenteric and mediastinal lymph nodes is determined by immunochemistry.
The following criteria is used for the scores:
0=lack of fluorescence
1=some fluorescent foci on some organ slides
2=approximately 1 foci per shot
3=wholly fluorescent organ.
A significant reduction of the virus load is observed in the immunized groups ($p \leq 4$ 0.05).

| | Mesenteric LN | | Virus load Mediastinal LN | | |
|---|---|---|---|---|---|
| Groups | mean | std | mean | std | N |
| Vaccinated | 0.5 | 0.6 | 1.3 | 0.2 | 8 |
| Controls | 1.8 | 0.8 | 2.0 | 0.8 | 8 |

Viral Excretion
The faecal swabs are assessed by PCR for PCV-2 shedding. The results are scored according the following criteria:
0=absence of PCV-2
1=presence of PCV-2

In the immunized group 38% of the piglets versus 88% in the control group excrete PCV-2 in the feces. The duration of viral excretion is significantly reduced in vaccinated group compared to controls.

| Groups | Mean duration of viral excretion (days) | | |
|---|---|---|---|
| | mean | std | N |
| Vaccinated | 1.2 | 2.1 | 8 |
| Controls | 11.4 | 6.3 | 8 |

It should be clearly understood that the invention defined by the appended claims is not limited to the specific embodiments indicated in the description above, but encompasses the variants which depart from neither the scope nor the spirit of the present invention.

| ANNEXE 1: Scores for clinical signs | |
|---|---|
| signs | score |
| Prostration | 0 no, 1 yes; 2 can't get up |
| vomitting | 0 no, 1 yes |
| dyspnea | 0 no, 1 moderate; 2 high |
| cough | 0 no, 1 yes |
| anorexia | 0 no, 1 yes |
| hyperthermia | 0 no, 1 ≧ 40° C.; 2 ≧ 41° C. |
| growing | 0 no, 1 DWG week x ≦ DWG week x − 1 and > 100 grams per day 2 DWG of the week ≦ 100 grams per day |
| death | 0 no, x score of the day just before the death |
| for a day the score is the sum of the score of each sign | |

| ANNEXE 2: Scores for macroscopic lesions | | |
|---|---|---|
| skin (color) | normal | 0 |
| | white | 1 |
| | yellow | 2 |
| corpulence | normal | 0 |
| | thin | 1 |
| | very thin | 2 |
| | cachectic | 3 |
| mucous | normal | 0 |
| | white | 1 |
| | yellow | 2 |
| sub. cut. Conjonctif | normal | 0 |
| | brillant | 1 |
| | yellow | 2 |
| ganglions (gg) | normal | 0 |
| | 1 large and or congestive | 1 |
| | >1 large and or congestive | 2 |
| | >1 very large | 3 |
| thoracic fluide | normal | 0 |
| | brillant | 1 |
| | visible | 2 |
| heart | normal | 0 |
| | lesion | 1 |
| lungs | normal | 0 |
| | lesion ≦ 4 | 1 |
| | lesion > 4 ≦ 6 | 2 |
| | lesion > 6 | 3 |
| pleura | normal | 0 |
| | lesion | 1 |
| ascite | normal | 0 |
| | brillant | 1 |
| | visible | 2 |
| peritoneum | normal | 0 |
| | lesion | 1 |
| stomach | normal | 0 |
| | lesion | 1 |
| | ulcer | 2 |
| small intestine | normal | 0 |
| | lesion | 1 |
| large intestine | normal | 0 |
| | lesion | 1 |
| Peyers plaques | normal | 0 |
| | visible on 1 part of the intestine | 1 |
| | visible on 2 part of the intestine | 2 |
| | very importante | 3 |
| liver | normal | 0 |
| | lesion | 1 |
| kidney | normal | 0 |
| | lesion | 1 |
| bladder | normal | 0 |
| | lesion | 1 |

We claim:

1. An immunogenic preparation comprising a complex of: at least one plasmid encoding and expressing in vivo in a porcine host an isolated nucleic acid molecule selected from the group consisting of open reading frame (ORF) 1 of porcine circovirus type II (PCV-2) and ORF2 of PCV-2; and, an adjuvant which comprises a cationic lipid of formula in which $R_1$ is a saturated or unsaturated linear aliphatic radical having from 12 to 18 carbon atoms, $R_2$ is aliphatic radical comprising from 2 to 3 carbon atoms, and X is an hydroxyl or amine group.

2. An immunogenic preparation comprising at least one plasmid encoding and expressing in vivo in a porcine host an isolated nucleic acid molecule selected from the group consisting of open reading frame (ORF) 1 of porcine circovirus II (PCV-2) and ORF2 of PCV-2; and, an adjuvant comprising a carbomer.

3. The immunogenic preparation according to claim 1, wherein the cationic lipid is N-(2-hydroxyethyl)-N,N-dimethyl-2,3-bis(tetradecyloxy)-1-propanammonium (DMRIE).

4. The immunogenic preparation according to claim 3, wherein DMRIE is coupled to a neutral lipid.

5. The immunogenic preparation according to claim 4, wherein DMRIE is coupled to dioleoylphosphatidylethanolamine (DOPE).

6. The immunogenic preparation according to any one of claims 1, 2, 3, 4 or 5 further comprising a porcine cytokine or a plasmid that encodes and expresses a porcine cytokine.

7. The immunogenic preparation according to claim 6, wherein the porcine cytokine is GM-CSF.

8. The immunogenic preparation according to claim 1 or 2, further comprising a plasmid encoding and expressing an immunogen from a porcine pathogenic agent other than PCV-2.

9. The immunogenic preparation according to any one of claims 1, 2, 3, or 4, wherein the preparation includes at least one plasmid that contains and expresses ORF1 of PCV-2.

10. The immunogenic preparation according to any one of claims 1, 2, 3, or 4, wherein the preparation includes at least one plasmid that contains and expresses ORF2 of PCV-2.

11. The immunogenic preparation according to any one of claims 1, 2, 3, or 4, wherein the preparation includes at least one plasmid that contains and expresses ORF1 and ORF2 of PCV-2.

12. The immunogenic preparation according to any one of claims 1, 2, 3, or 4, wherein the preparation includes at least two plasmids, one that contains and expresses ORF1 of PCV2, and one that contains and expresses ORF2 of PCV-2.

13. The immunogenic preparation of claim 5 wherein the DMRIE:DOPE molar ratio ranges from 95:5 to 5:95.

14. The immunogenic preparation of claim 13 wherein the DMRIE:DOPE molar ratio is 1:1.

15. The immunogenic preparation of claim 3 wherein the plasmid:DMRIE weight ratio ranges from 50:1 to 1:10.

16. The immunogenic preparation of claim 3 wherein the plasmid:DMRIE weight ratio ranges from 10:1 to 1:5.

17. The immunogenic preparation of claim 3 wherein the plasmid:DMRIE weight ratio ranges from 1:1 to 1:2.

18. The immunogenic preparation of claim 5 wherein the plasmid:DMRIE-DOPE weight ratio ranges from 50:1 to 1:10.

19. The immunogenic preparation of claim 5 wherein the plasmid:DMRIE-DOPE weight ratio ranges from 10:1 to 1:5.

20. The immunogenic preparation of claim 5 wherein the plasmid:DMRIE-DOPE weight ratio ranges from 1:1 to 1:2.

21. The immunogenic preparation of claim 6 wherein the preparation includes a plasmid that encodes and expresses a porcine cytokine which is GM-CSF.

22. A method for eliciting an immunogenic response in a porcine host against porcine circovirus comprising administering to the porcine host the immunogenic preparation of any one of claim 1, 2, 3 or 4.

23. A method for enhancing a host immunogenic response, in a porcine host, to a polypeptide encoded by open reading frame (ORF) 1 of porcine circovirus type II (PCV-2) or ORF2 of PCV-2, said method comprising administering to the porcine host at least one plasmid that encodes and expresses ORF1 of PCV-2 or ORF2 of PCV-2, when the plasmid is complexed with a adjuvant which comprises a cationic lipid of formula in which $R_1$ is a saturated or unsaturated linear aliphatic radical having from 12 to 18 carbon atoms, $R_2$ is aliphatic radical comprising from 2 to 3 carbon atoms, and X is an hydroxyl or amine group.

24. A method for enhancing a host immune response, in a porcine host, to a polypeptide encoded by open reading frame (ORF) 1 of porcine circovirus type II (PCV-2) or ORF2 of PCV-2, said method comprising administering to the porcine host at least one plasmid that encodes and expresses ORF1 of PCV-2 or ORF2 of PCV-2, and an adjuvant which comprises a carbomer.

25. The method of claim 23 wherein the cationic lipid is N-(2-hydroxyethyl)-N,N-dimethyl-2,3-bis(tetradecyloxy)-1-propanammonium (DMRIE).

26. The method of claim 25 wherein DMRIE is coupled to a neutral lipid.

27. The method of claim 26 wherein DMRIE is coupled to dioleoylphosphatidylethanolamine (DOPE).

28. The method of any one of claims 23 or 24 wherein the administering includes administering a porcine cytokine or a plasmid that encodes and expresses a porcine cytokine.

29. The method of claim 28 wherein the porcine cytokine is GM-CSF.

30. The method according to claim 23 or 24, wherein the administering includes administering a plasmid encoding and expressing an immunogen from a porcine pathogenic agent other than PCV-2.

31. The method according to any one of claims 23 or 24 wherein the administering includes administering at least one plasmid that contains and expresses ORF1 of PCV-2.

32. The method according to any one of claims 23 or 24 wherein the administering includes administering at least one plasmid that contains and expresses ORF2 of PCV-2.

33. The method according to any one of claims 23 or 24 wherein the administering includes administering at least one plasmid that contains and expresses ORF1 and ORF2 of PCV-2.

34. The method according to any one of claim 23 or 24, wherein the administering includes administering at least tow plasmids, one that contains and expresses ORF1 of PCV-2, and one that contains and expresses ORF2 of PCV-2.

35. The method of claim 27 wherein the DMRIE:DOPE molar ratio ranges from 95:5 to 5:95.

36. The method of claim 27 wherein the DMRIE:DOPE molar ratio is 1:1.

37. The method of claim 25 wherein the plasmid:DMRIE weight ratio ranges from 50:1 to 1:10.

38. The method of claim 25 wherein the plasmid:DMRIE weight ratio ranges from 10:1 to 1:5.

39. The method of claim 25 wherein the plasmid:DMRIE weight ratio ranges from 1:1 to 1:2.

40. The method of claim 27 wherein the plasmid:DMRIE-DOPE weight ratio ranges from 50:1 to 1:10.

41. The method of claim 27 wherein the plasmid:DMRIE-DOPE weight ratio ranges from 10:1 to 1:5.

42. The method of claim 27 wherein the plasmid:DMRIE-DOPE weight ration ranges from 1:1 to 1:2.

43. The method of claim 28 wherein the administering includes administering a plasmid that encodes and expresses a porcine cytokine which is GM-CSF.

44. The method of claim 23 or 24 wherein the administering is intramuscularly.

45. The method of claim 23 or 24 wherein the administering is intradermally.

46. The method of claim 22 wherein the administering is intramuscularly.

47. The method of claim 22 wherein the administering is intradermally.

* * * * *

UNITED STATES PATENT AND TRADEMARK OFFICE
CERTIFICATE OF CORRECTION

PATENT NO. : 6,943,152 B1
DATED : September 13, 2005
INVENTOR(S) : Jean-Christophe Francis Audonnet et al.

It is certified that error appears in the above-identified patent and that said Letters Patent is hereby corrected as shown below:

Title page,
Item [75], Inventors, replace "Francis Jean-Christophe Audonnet" with -- Jean-Christophe Francis Audonnet --.

Column 21,
Line 22, replace "immunogenic" with -- immune --.
Line 28, replace "a adjuvant" with -- an adjuvant --.

Column 22,
Line 22, replace "tow" with -- two --.

Signed and Sealed this

Sixth Day of December, 2005

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer JP779

<400> SEQUENCE: 1
catcatcatg tcgacatgac gtatccaagg aggcg                           35

<210> SEQ ID NO 2
<211> LENGTH: 36
<212> TYPE: DNA
<213> ORGANISM: Artificial Sequence
```

```
<220> FEATURE:
<221> NAME/KEY: misc_feature
<222> LOCATION: (1)..(36)
<223> OTHER INFORMATION: primer JP780

<400> SEQUENCE: 2
tactactaca gatctttagg gtttaagtgg ggggtc                               36

<210> SEQ ID NO 3
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer JP781

<400> SEQUENCE: 3
catcatcatg tcgacatgcc cagcaagaag aatgg                                35

<210> SEQ ID NO 4
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer JP782

<400> SEQUENCE: 4
tactactaca gatcttcagt aatttatttc atatgg                               36

<210> SEQ ID NO 5
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer JP783

<400> SEQUENCE: 5
catcatcatg tcgacatgac gtggccaagg aggcg                                35

<210> SEQ ID NO 6
<211> LENGTH: 40
<212> TYPE: DNA
<213> ORGANISM: Artificial Sequence
<220> FEATURE:
<221> NAME/KEY: misc_feature
<222> LOCATION: (1)..(40)
<223> OTHER INFORMATION: primer JP784

<400> SEQUENCE: 6
tactactaca gatctttatt tatttagagg gtcttttagg                           40

<210> SEQ ID NO 7
<211> LENGTH: 35
<212> TYPE: DNA
<213> ORGANISM: Artificial Sequence
<220> FEATURE:
<221> NAME/KEY: misc_feature
<222> LOCATION: (1)..(35)
<223> OTHER INFORMATION: primer JP785

<400> SEQUENCE: 7
catcatcatg tcgacatgcc aagcaagaaa agcgg                                35
```

```
<210> SEQ ID NO 8
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer JP786

<400> SEQUENCE: 8
tactactaca gatcttcagt aatttatttt atatgg                                36

<210> SEQ ID NO 9
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer RG972

<400> SEQUENCE: 9
tatgcggccg ccaccatgtg gctgcagaac ctg                                    33

<210> SEQ ID NO 10
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: primer RG973

<400> SEQUENCE: 10
tatgcggccg ctacgtatca cttctgggct ggtt                                   34
```